(12) United States Patent
Xuan

(10) Patent No.: US 11,699,578 B2
(45) Date of Patent: Jul. 11, 2023

(54) METHOD OF MASS SPECTROMETRY

(71) Applicant: Thermo Fisher Scientific (Bremen) GmbH, Bremen (DE)

(72) Inventor: Yue Xuan, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 17/095,153

(22) Filed: Nov. 11, 2020

(65) Prior Publication Data

US 2021/0225627 A1 Jul. 22, 2021

(30) Foreign Application Priority Data

Nov. 13, 2019 (GB) ...................................... 1916524

(51) Int. Cl.
*G01N 30/72* (2006.01)
*H01J 49/00* (2006.01)

(52) U.S. Cl.
CPC ........ *H01J 49/0036* (2013.01); *G01N 30/724* (2013.01); *H01J 49/0031* (2013.01); *H01J 49/0045* (2013.01)

(58) Field of Classification Search
CPC .............. H01J 49/0031; H01J 49/0036; H01J 49/0045; G01N 30/724
USPC ...................................................... 250/282
See application file for complete search history.

(56) References Cited

U.S. PATENT DOCUMENTS

| | | | |
|---|---|---|---|
| 8,809,770 B2* | 8/2014 | Bonner | H01J 49/42 250/281 |
| 9,252,003 B2* | 2/2016 | Hermanson | H01J 49/0027 |
| 9,911,585 B1* | 3/2018 | Zabrouskov | H01J 49/0031 |
| 10,591,448 B2* | 3/2020 | Astarita | H01J 49/0036 |
| 10,653,710 B2* | 5/2020 | Agresta | A61K 45/06 |
| 11,289,318 B2* | 3/2022 | Zhou | H01J 49/0027 |
| 2016/0154006 A1* | 6/2016 | Hermanson | H01J 49/0027 250/288 |
| 2018/0233341 A1* | 8/2018 | McAlister | H01J 49/4215 |
| 2021/0311072 A1* | 10/2021 | Hermanson | H01J 49/26 |
| 2022/0181132 A1* | 6/2022 | Bonner | H01J 49/0036 |
| 2022/0397578 A1* | 12/2022 | Slavov | G01N 33/6842 |
| 2023/0020894 A1* | 1/2023 | Chiarle | C07K 16/2818 |

* cited by examiner

*Primary Examiner* — Wyatt A Stoffa

(57) ABSTRACT

Disclosed are techniques for mass spectrometry. In one example, an isotopologue of a target analyte is added to a sample. The sample and isotopologue are analyzed as it elutes from a chromatography system to form precursor ions. The precursor ions are mass analysed using a data independent acquisition (DIA) methodology comprising performing mass analysis scans in the MS1 domain and performing mass analysis scans in the MS2 domain. Upon identifying that the isotopologue is eluting from the chromatography system, a plurality of target scans are performed, each having a target isolation window including a mass to charge ratio representative of the target analyte over the duration of a chromatographic peak of the isotopologue for at least one of identification and quantitation of the target analyte. The target scans are configured to provide additional quantitation data for the target analyte.

23 Claims, 5 Drawing Sheets

METHOD OF MASS SPECTROMETRY

CROSS-REFERENCE TO RELATED APPLICATIONS

This application claims the priority to GB Patent Application No. 1916524.0, filed on Nov. 13, 2019, which is hereby incorporated herein by reference in its entirety.

FIELD OF THE DISCLOSURE

The present invention relates to a method of mass spectrometry and a mass spectrometer for performing a method of mass spectrometry. In particular, the present invention relates to a method of data independent acquisition (DIA) mass spectrometry and a mass spectrometer for performing the same.

BACKGROUND

Mass spectrometry is a long established technique for identification and quantitation of often complex mixtures of large organic molecules. In recent years, techniques have been developed that allow analysis of a wide range of biological and non-biological materials, with applications across the fields of law enforcement, environmental, scientific research, and biology. For example, in proteomics, simple and complex mixtures of proteins can be analysed, with applications in drug discovery, disease identification and so forth.

Proteins, comprising large numbers of amino acids, are typically of significant molecular weight. Accordingly, accurate identification and quantitation of the protein by direct mass spectrometric measurement is challenging. It is thus well known to carry out fragmentation of the precursor sample material. A variety of fragmentation techniques are known, which may result in the generation of different fragment ions from the precursor ions. Moreover, the fragmentation mechanism may be affected by different applied fragmentation energies.

Analysis of samples can be broadly separated into data dependent acquisition (DDA) methodologies and data independent acquisition (DIA) methodologies. DDA seeks to confirm that one or more species is/are present in a given sample. Methods of DDA identify a fixed number of precursor ions species, and select and analysis those via tandem mass spectrometry. The determination of which precursor ion species are of interest in DDA may be based upon intensity ranking (for example, the top ten most abundant species as observed by peaks in a precursor mass spectrum, hereafter referred to as MS1) or by defining an inclusion list of precursor mass spectral peeks for example by user selection, from which fragment spectra hereafter referred to as MS2 are always acquired regardless of the intensity ranking of the peak in the precursor mass spectrum MS1.

By contrast DIA seeks to determine what is present in a sample of potentially unknown identity. To determine the molecular structure of unknown sample molecules, a combination of broad mass range MS1 scans and a set of MS2 scans may be provided. DIA avoids the decisions necessary in DDA, by simply dividing the mass range of interest (typically user defined) into segments and obtaining MS2 spectra for each segment. With DIA, the acquisition of an MS1 precursor spectrum becomes more or less optional, since the parameters of the precursor selection window themselves carry information about the range of possible precursor ions.

DIA methodologies are of particular relevance for recording a substantial proportion of the information from the sample and can be used for targeted therapeutics applications. In particular, DIA methodologies may provide high-throughput, reproducible, and sensitive workflows for the analysis of clinical markers, cancer mutations and/or sequence variants from the gene level and the protein/peptide level. This in turn helps to understand the disease mechanism in the Proteogenomics research, as well as providing additional information for guiding clinical decisions.

For example, GB 1701857.3 (published as GB 2559395 A) discloses a data independent acquisition method of mass spectrometry for analysing a sample. The DIA methodology provides high resolution identification and quantitation of a sample in the MS1 domain (i.e. with precursor unfragmented ions). As a result of the relatively high resolution used in the MS1 domain scans it is possible to distinguish between two different sample molecules with low mass differences, for example an MS1 scan resolution of 120,000 is capable of distinguishing between peptides with around 30 ppm (parts per million) mass difference. The methodology also uses a cycle of MS2 spectra, at a relatively lower resolution, to provide a secondary confirmation of preliminary identification based on the analysis of MS1 data. The MS1 scans are interspersed throughout the MS2 scans and the MS1 repetition rate is set (independently of the MS2 cycle time) such that a sufficient number of data points are acquired over a chromatographic peak for accurate quantitation from the chromatographic peak area.

SUMMARY OF THE INVENTION

According to a first aspect of the disclosure a method of mass spectrometry is provided. The method comprises:
a) adding an isotopologue of a target precursor to a sample;
b) ionising the sample and isotopologue as it elutes from a chromatography system;
c) mass analysing the sample using a data independent acquisition (DIA) methodology comprising performing mass analysis scans in the MS1 domain and performing mass analysis scans in the MS2 domain.

Upon identifying that the isotopologue is eluting from the chromatography system, the method further comprises performing target scans having a target isolation window including a mass to charge ratio representative of the target precursor over the duration of a chromatographic peak of the isotopologue for at least one of identification and quantitation of the target precursor, wherein the target scans are configured to provide additional quantitation data for the target analyte. The target scans have a target isolation window that is on the order of the width of isolation window of the mass analysis scans in the MS2 domain of the DIA methodology, preferably narrower, and preferably less than 10 Da.

The method of the first aspect performs target scans which have an isolation window which is selected for the identification and/or quantitation of a target analyte. It will be appreciated that a target analyte may sometimes be present in a sample in a low quantity, thereby making it challenging to detect. In particular, for a given sample, the retention time of a targeted analyte may not be known prior to performing the DIA methodology. As the targeted analyte may only be present in the sample in low quantities, it is challenging to determine the retention time using conventional methods. Accordingly, an isotopologue is added to the sample. An isotopologue is a molecule that differs from its parent molecule in that at least one atom has a different number of neutrons. As the isotopologue has the same chemical structure as the target analyte of interest, the retention time of the isotopologue will be similar to the target analyte. However, the isotopologue can be distinguished from the target analyte in a mass analysis scan due to the different number of neutrons.

Accordingly, the method of the first aspect may provide a series of target scans in addition to the MS1 and MS2 scans of the DIA methodology. For example, the target scans may be performed in the MS1 domain and/or the MS2 domain. In some embodiments, the target scans may comprise target Selected Ion Monitoring (SIM) scans and/or target MS2 scans. The target scans are performed upon identifying that isotopologue is eluting from the chromatography system. Accordingly, the method of the first aspect may provide target scans which may be suitable for identification of relatively low abundance target precursors as part of a DIA methodology. Upon detection of the isotopologue the target scans are performed over a duration of the chromatographic peak of the isotopologue which generally corresponds to the chromatographic peak of the target analyte. As the target scans are performed upon identification of the isotopologue, the target scans may be performed in such a manner that the overall cycle time of the method of mass spectrometry is not significantly increased.

In some embodiments, the target scans may comprise a plurality of target MS2 scans and/or a plurality of target SIM scans. Target MS2 scans are mass analysis scans which are performed having a target isolation window including a mass to charge ratio representative of the target analyte, wherein the mass analysis scan is performed in the MS2 domain. Target SIM scans are mass analysis scans which are performed having a target isolation window including a mass to charge ratio representative of the target analyte, wherein the mass analysis scan is performed in the MS1 domain. The target scans, whether target MS2 scans or target SIM scans, have a target isolation window that is on the order of the width of isolation window of the mass analysis scans in the MS2 domain of the DIA methodology, preferably narrower, and preferably less than 10 Da, less than 8 Da, less than 6 Da, less than 4 Da, or less than 2 Da.

In some embodiments, identifying that the isotopologue is eluting from the chromatography system comprises identifying that the isotopologue is eluting using the data from the MS1 scan. By using the MS1 scan to identify the isotopologue, it may be inferred that the target analyte is eluting from the chromatography system thereby triggering the target scans according to the method of the first aspect. In some embodiments, identifying that the isotopologue is eluting from the chromatography system comprises identifying that the isotopologue is eluting using data from the mass analysis scans in the MS2 domain in addition to the MS1 scan.

In some embodiments, performing each target MS2 scan comprises mass selecting the analyte ions based on the target isolation window and fragmenting the precursor ions within the target isolation window to form target fragmented ions, and mass analysing the target fragmented ions.

In some embodiments, each target MS2 scan has a target isolation window which includes a mass to charge ratio representative of the target analyte and a mass to charge ratio representative of the isotopologue. As such, MS2 mass analysis of the isotopologue ions may be combined with MS2 mass analysis of the target analyte. The target isolation window may effectively be a continuous isolation window which includes mass to charge ratios representative of the target analyte and mass to charge ratios representative of the isotopologue. As such a single mass isolation window may be provided to mass select both ions representative of the target analyte and the isotopologue. The mass selected target analyte and isotopologue ions can be fragmented together to provide target fragmented ions and isotopologue fragmented ions, which are then mass analysed together.

In some embodiments, upon identifying that the isotopologue is eluting from the chromatography system, the method further comprises performing isotopologue scans having an isotopologue isolation window including a mass to charge ratio representative of the isotopologue over the duration of a chromatographic peak of the isotopologue for quantitation of the isotopologue. The isotopologue scans may comprise at least one of: a plurality of isotopologue SIM scans and a plurality of isotopologue MS2 scans. Accordingly, the method according to the first aspect may provide a plurality of target scans which may characterise the chromatographic peak of the target analyte, and a plurality of isotopologue scans which may characterise the chromatographic peak of the isotopologue. As such, the method according to the first aspect may establish calibration curves over the duration of the chromatographic peak for each of the target precursor and the isotopologue. Establishing calibration curves for the target analyte and the isotopologue may be used to provide further identification and quantitation of the target analyte and/or isotopologue.

In some embodiments, adding an isotopologue of a target analyte to the sample comprises adding a first amount of a first isotopologue of the target analyte having a first mass to the sample, and adding a second amount of a second isotopologue of the target analyte having a second mass to the sample, the second amount and the second mass different being different to the first amount and the first mass respectively. The first and second amounts are known and can therefore provide known concentrations of the first and second isotopologues in the sample. Upon identifying that at least one of the first or second isotopologues is eluting from the chromatography system, the method comprises performing a plurality of first isotopologue scans having a first isotopologue isolation window including a mass to charge ratio representative of the first isotopologue, performing a plurality of second isotopologue scans having a second isotopologue isolation window including a mass to charge ratio representative of the second isotopologue, and generating a quantitation calibration from the first isotopologue scans, the second isotopologue scans, and the target scans. The plurality of first isotopologue scans and the plurality of second isotopologue scans may each comprise isotopologue MS2 scans and/or isotopologue SIM scans. It will be appreciated that the peak intensities of the fragments in the first and second isotopologue scans will reflect the different amounts of the first and second isotopologues added to the sample. Accordingly, the first and second isotopologues can be used to establish a calibration curve for the method of mass spectrometry. The data from the first and second isotopologue scans may be combined with the target scan data to determine a quantitation calibration for the target analyte and thus quantify the target analyte with improved accuracy.

In some embodiments, performing each isotopologue MS2 scan comprises mass selecting the precursor ions based on the isotopologue isolation window and fragmenting the precursor ions within the isotopologue isolation window to form isotopologue fragmented ions, and mass analysing the isotopologue fragmented ions.

In some embodiments, the isolation window for each target scan may be different to the isolation window for each isotopologue scan. It will be appreciated that the mass to charge ratio of target analyte ions will be different to the mass to charge ratio of isotopologue ions. Accordingly, different isolation windows for the isotopologue ions and the target ions may be provided in order to ensure that the respective target scans and isotopologue scans are selective. For example, by providing selective target MS2 scans and isotopologue MS2 scans the sensitivity and accuracy of the method of mass spectrometry may be improved.

In some embodiments, each target MS2 scan performed may be multiplexed with a respective isotopologue MS2 scan. As such, the ions selected by the target isolation window for a target MS2 scan may be combined with the ions selected using the isotopologue isolation window for a respective isotopologue MS2 scan. The combined ions may then be fragmented and mass analysed together in a single mass analysis scan. Such multiplexing of the target MS2 scans and isotopologue MS2 scans may further reduce the cycle time of the method of mass spectrometry.

In some embodiments, multiplexing a target MS2 scan with an isotopologue MS2 scan comprises: combining the precursor ions within the target isolation window for each target MS2 scan with the precursor ions within the isotopologue isolation window to form multiplexed precursor ions, fragmenting the multiplexed precursor ions to form multiplexed fragmented ions, and mass analysing the multiplexed fragmented ions. The precursor ions within the target isolation window may be combined with the precursor ions within the isotopologue isolation window in an ion storage device and stored there as multiplexed precursor ions. The multiplexed precursor ions may be fragmented to form multiplexed fragmented ions, for example by ejecting the multiplexed precursor ions to a fragmentation device, such as a collision cell. In some embodiments, multiplexing a target MS2 scan with an isotopologue MS2 scan comprises: fragmenting precursor ions within the target isolation window for each target MS2 scan to form target fragmented ions, fragmenting precursor ions within the isotopologue isolation window to form isotopologue fragmented ions, combining the target and isotopologue fragmented ions to form multiplexed fragmented ions, and mass analysing the multiplexed fragmented ions. The multiplexed fragmented ions may be combined and stored in an ion storage device, before mass analysing the multiplexed fragmented ions.

In some embodiments, each target SIM scans may be multiplexed with an isotopologue SIM scan. In some embodiments, multiplexing a target SIM scan with an isotopologue SIM scan comprises combining the precursor ions within the target isolation window for each target SIM scan with the precursor ions within the isotopologue isolation window to form multiplexed precursor ions, and mass analysing the multiplexed precursor ions.

In some embodiments, the target scans are interleaved throughout the DIA methodology over the duration of the chromatographic peak of the isotopologue. In some embodiments, the isotopologue scans may be interleaved throughout the DIA methodology over the duration of the chromatographic peak of the isotopologue. As such, the target scans may be distributed over the duration of the chromatographic peak of the isotopologue which generally corresponds to the chromatographic peak of the target analyte. In some embodiments, the chromatographic peaks of the target analyte and isotopologue may have the same shape and time. In some embodiments, the heavier molecule may have a chromatographic peak which lags behind the chromatographic peak of the lighter molecule. The amount of lag may be determined prior to performing the method of mass spectrometry and taken into account. In many cases, the amount of lag is relatively insignificant such that a substantial proportion (e.g. at least 50%) of the duration of the isotopologue chromatographic peak overlaps with the duration of the target analyte chromatographic peak. For example, it may be helpful to know the lag for quantitation of the target analyte to improve the scheduling of the target scans to more closely correspond to the chromatographic peak of the target analyte.

In some embodiments, the target scans and/or the isotopologue scans are interleaved throughout the DIA methodology at intervals of no greater than 2 seconds. In some embodiments, the target scans are performed at least 6 times per chromatographic peak in order to obtain more accurate quantitation data for the target analyte.

In some embodiments, the target isolation window for each target MS2 scan is no greater than 5 Da. In some embodiments, the isotopologue isolation window for each isotopologue MS2 scan is no greater than 5 Da. In some embodiments, the target isolation window and/or the isotopologue isolation window may be no greater than 4 Da, 3 Da, or 2 Da. In some embodiments, the target isolation window for a target analyte ions may be dependent on the mass to charge ratio of the target analyte ion, wherein target analyte ions with higher charge may have a narrower isolation window. By providing isolation windows which are relatively narrow, other precursor ions may be excluded from the additional MS2 scans. This in turn may improve the signal to noise ratio of the target analyte/isotopologue ions in the MS2 spectra. Furthermore, excluding other precursor ions from the additional MS2 scans may simplify subsequent analysis of the target MS2 scan data.

In some embodiments, mass analysing the sample using a data independent acquisition (DIA) methodology comprises performing a plurality of MS1 scans of the precursor ions; and performing a plurality of MS2 scans of the precursor ions. Various DIA methodologies are known to the skilled person. It will be appreciated that the additional MS2 scans (target MS2 scan and/or isotopologue MS2 scan) are to be performed in addition to the scans of the DIA methodology. The MS2 scans of the DIA methodology may generally each be performed for a different mass range segment or isolation window of the precursor mass range of interest such that a set of MS2 scans of the DIA methodology covers the precursor mass range of interest. The DIA methodology, and the method of the first aspect may be performed on any known mass spectrometer configured to perform DIA acquisition. In particular, the method of the first aspect may be performed on a mass spectrometer comprising an orbital trapping mass analyser, a tandem mass spectrometer comprising two mass analysers etc.

In some embodiments, mass analysing the sample using a DIA methodology comprises;

selecting a precursor mass range of interest for the sample to be analysed;

performing a plurality of MS1 scans, each of the MS1 scans comprising:

mass analysing the precursor ions across the precursor mass range of interest, using a mass analyser operated at a first, relatively higher resolution of at least 50,000 at m/z=200 amu, for identification and/or quantitation of the sample in the MS1 domain across the precursor mass range of interest; and performing a set of MS2 scans by:

segmenting the precursor mass range of interest into a plurality of precursor mass range segments, wherein for each precursor mass range segment:
fragmenting the precursor ions within that mass range segment, and
performing an MS2 scan of the fragmented mass range segment with the mass analyser, operated at a second, relatively lower resolution, such that each of the fragmented sample segments across the precursor mass range of interest is fragmented and scanned in the MS2 domain,
wherein the performing of the MS1 scans are interleaved throughout the performing of each of the sets of MS2 scans such that the MS1 scans provide a mass chromatogram of the sample.

Such a DIA methodology is disclosed in GB 2559395 A and further refinements of the methodology are described therein. The entire contents of GB 2559395 A are hereby incorporated by reference.

According to the DIA methodology discussed above, a plurality of MS1 scans of the precursor ions are performed across a precursor mass range of interest, such that each MS1 scan is suitable for quantitation and/or identification of the sample in the MS1 domain across the entire precursor mass range of interest. As such, it is understood that each of the MS1 scans extends across substantially all of the precursor mass range of interest.

The MS1 scans are performed using a mass analyser operated at a first, relatively higher resolution, for quantitation of the sample in the MS1 domain across the mass range of interest. As such, the relatively high resolution of the mass analyser is a resolution which is selected in order to reduce or minimise, and most preferably eliminate, interferences from matrix or other sample ions in the MS1 scan, thereby allowing identification and quantitation of the precursor sample ions in the MS1 domain. The relatively high resolution of the MS1 scans are performed at a resolution of at least 50,000 in order to sufficiently distinguish between precursor ions with similar masses, such that accurate quantitation and/or identification may be performed in the MS1 domain According to the above DIA methodology, the MS1 scans may be performed a plurality of times, interleaved with the performance of the set of MS2 scans. As such, the MS1 scans are repeated a number of times throughout the performance of a set of MS2 scans in order to repeatedly sample the precursor ions in the MS1 domain over the duration of a chromatographic peak. The plurality MS1 scans and at least one set of MS2 scans (but preferably not more than two sets) is performed within the time period based on the width of the chromatographic peak (e.g. FWHM). In some embodiments, the number of MS1 scans performed is at least twice as many, or at least three times as many, as the number of sets of the MS2 scans performed. Thus, the MS1 scans provide a mass chromatogram of the sample as it elutes from the chromatographic system. Preferably the MS1 scans are performed at least 3 times, more preferably at least 5 times and most preferably at least 7 times over the duration of a set of MS2 scans. By repeating the MS1 scan a number of times a more accurate quantitation of the precursor ions can be established. As such, the MS1 scans may be repeated in order to sample the precursor ions a number of times.

In some embodiments, the mass analyser used to perform the at least one of the MS1 and MS2 scans is an orbital trapping mass analyser. Advantageously, by using an orbital trapping mass analyser MS1 scans may be performed with a relatively high resolution and a set of MS2 scans may be performed with a relatively low resolution, whilst using a relatively compact mass analyser.

In some embodiments, the orbital trapping analyser is used to perform MS1 scans forming part of the DIA methodology with a resolution of at least 50,000 in order to provide improved quantitation of precursor ions in the MS1 domain. For example, a relatively high resolution for the orbital mass trapping analyser according to the present invention may be at least 100,000, and a relatively low resolution (for the MS2 scans) may be less than 60,000, or less than 50,000, or less than 40,000, more preferably less than 30,000. In some embodiments, resolutions for the MS2 scans of less than 20,000, or less than 15,000, or less than 10,000 (e.g. 7,500) may be sufficient, thereby enabling narrower mass range segments to be used, which assists in validating the identification/quantitation of the precursor ions. Accordingly, an orbital trapping mass analyser may be used in the present method to optimise the resolution of the MS1 scans to quantitate the precursor ions, while the resolution of the MS2 scans are optimised to validate the quantitation of the precursor ions.

Although an orbital trapping mass analyser may be used to perform MS1 scans with a relatively high resolution of at least 100,000, the skilled person will appreciate that other mass analysers with a resolution of at least 100,000 may also be suitable for use in the method of the first aspect. For example, a multi-reflection time-of-flight (MR-ToF) mass analyser or a Fourier transform Ion Cyclotron Resonance (FT-ICR) mass analyser can be used. The high mass accuracy of the orbital trapping mass analyser or FT-ICR mass analyser enables high reliability of identification of samples from the MS1 scans, with the MS2 scans providing confirmation of identification. In some embodiments, a mass analyser (e.g. an orbital trapping mass analyser) may be used to perform MS1 scans with a relatively high resolution of at least 120,000, or at least 130,000, or at least 140,000 or at least 150,000. By increasing the resolution of the MS1 scans, the ability to distinguish between various sample ions and matrix ions is improved, thereby improving the accuracy of the sample quantitation.

According to a second aspect of the disclosure, a mass spectrometer is provided. The mass spectrometer is for performing data independent acquisition mass spectrometry on a sample to which an isotopologue of a target analyte is added. The mass spectrometer comprises an ionisation source for producing a plurality of precursor ions, a mass analyser, a fragmentation apparatus, a mass selector, a chromatography system configured to separate molecules of the sample upstream from the mass selector; and a controller. The controller is configured:
to cause the ionisation source to ionise the sample and isotopologue as they elute from a chromatography system to form precursor ions;
to cause the mass spectrometer to mass analyse the precursor ions using a data independent acquisition (DIA) methodology comprising performing mass analysis scans in the MS1 domain and performing mass analysis scans in the MS2 domain;
to identify if the isotopologue is eluting from the chromatography system, upon which the controller is further configured
to cause the mass spectrometer to perform a plurality of target scans each having a target isolation window including a mass to charge ratio representative of the target analyte over a duration of a chromatographic peak of the isotopologue for at least one of identification and quantitation of the target analyte, wherein the target scans are configured to provide additional quantitation data for the target analyte.

Accordingly, it will be appreciated that the mass spectrometer of the second aspect may be configured to perform the method of the first aspect of the disclosure.

In some embodiments, the controller of the mass spectrometer may be further configured to cause the mass spectrometer to any of the further optional features of the method of the first aspect outlined above.

According to a third aspect of the disclosure, a computer program is provided. The computer program comprises instructions to cause the mass spectrometer of the second aspect to execute the method according to the first aspect of the disclosure.

According to a fourth aspect of the disclosure, a computer readable medium is provided. The computer readable medium has stored thereon the computer program of the third aspect.

BRIEF DESCRIPTION OF THE DRAWINGS

The invention may be put into practice in a number of ways and a specific embodiment will now be described by way of example only and with reference to the Figures in which.

DETAILED DESCRIPTION

In the present disclosure, reference is made to resolutions of a mass analyser. All resolutions referenced in this disclosure will be understood by the skilled person to refer to a resolution of a mass analyser at a mass to charge ratio (m/z) equal to 200 amu (m/z=200 amu). The skilled person will understand that the m/z ratio at which the resolution of the mass analyser is specified is merely indicative of the resolution of the mass analyser at that m/z value, and is not tied to the m/z range over which the mass analyser is scanned according to the methodology of the present invention.

Figure 1:
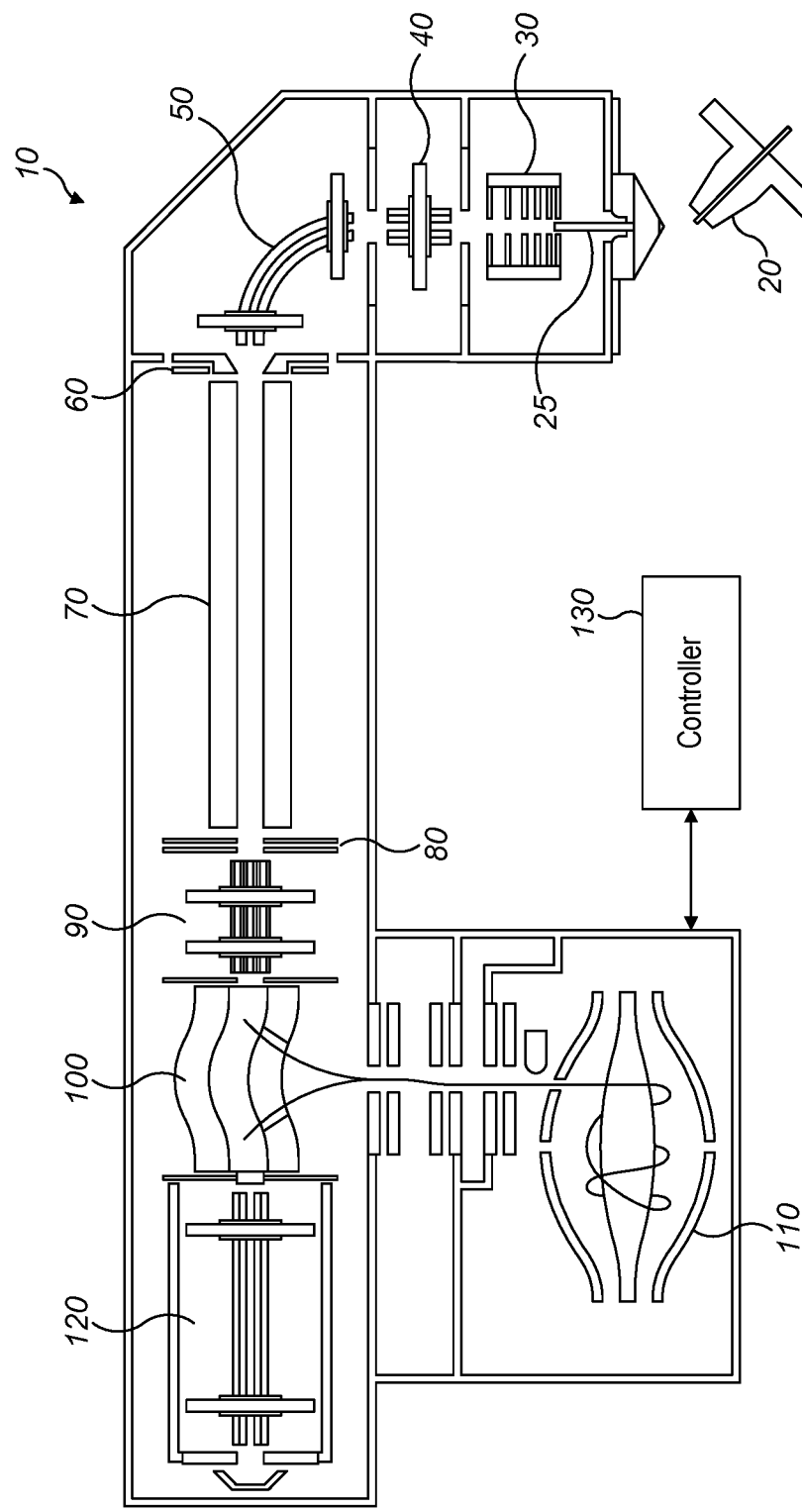
FIG. 1 shows a schematic arrangement of a mass spectrometer suitable for carrying out methods in accordance with embodiments of the present disclosure.

FIG. 1 shows a schematic arrangement of a mass spectrometer 10 suitable for carrying out methods in accordance with embodiments of the present invention. The arrangement of FIG. 1 represents, schematically, the configuration of the Q-Exactive® mass spectrometer from Thermo Fisher Scientific, Inc.

In FIG. 1, a sample to be analysed is supplied (for example from an autosampler) to a chromatographic apparatus such as a liquid chromatography (LC) column (not shown in FIG. 1). One such example of an LC column is the Thermo Fisher Scientific, Inc ProSwift monolithic column which offers high performance liquid chromatography (HPLC) through the forcing of the sample carried in a mobile phase under high pressure through a stationary phase of irregularly or spherically shaped particles constituting the stationary phase. In the HPLC column, sample molecules elute at different rates according to their degree of interaction with the stationary phase.

A chromatograph may be produced by measuring over time the quantity of sample molecules which elute from the HPLC column using a detector (for example a mass spectrometer). Sample molecules which elute from the HPLC column will be detected as a peak above a baseline measurement on the chromatograph. Where different sample molecules have different elution rates, a plurality of peaks on the chromatograph may be detected. Preferably, individual sample peaks are separated in time from other peaks in the chromatogram such that different sample molecules do not interfere with each other On a chromatograph, a presence of a chromatographic peak corresponds to a time period over which the sample molecules are present at the detector. As such, a width of a chromatographic peak is equivalent to a time period over which the sample molecules are present at a detector. Preferably, a chromatographic peak has a Gaussian shaped profile, or can be assumed to have a Gaussian shaped profile. Accordingly, a width of the chromatographic peak can be determined based on a number of standard deviations calculated from the peak. For example, a peak width may be calculated based on 4 standard deviations of a chromatographic peak. Alternatively, a peak width may be calculated based on the width at half the maximum height of the peak. Other methods for determining the peak width known in the art may also be suitable. As such, the MS1 data acquired according to the DIA method of the invention thus provides a mass-chromatogram of the sample eluted from the column.

The sample molecules thus separated via liquid chromatography are then ionized using an electrospray ionization source (ESI source) 20 which is at atmospheric pressure. It will be appreciated by those skilled in the art that other suitable types of ionization source may be used, such as atmospheric pressure chemical ionization (AFCI), thermospray ionization etc. Sample ions then enter a vacuum chamber of the mass spectrometer 10 and are directed by a capillary 25 into an RF-only S lens 30. The ions are focused by the S lens 30 into an injection flatpole 40 which injects the ions into a bent flatpole 50 with an axial field. The bent flatpole 50 guides (charged) ions along a curved path through it whilst unwanted neutral molecules such as entrained solvent molecules are not guided along the curved path and are lost.

An ion gate (TK lens) 60 is located at the distal end of the bent flatpole 50 and controls the passage of the ions from the bent flatpole 50 into a downstream quadrupole mass filter 70. The quadrupole mass filter 70 is typically but not necessarily segmented and, when operated in a selective mode, serves as a band pass filter, allowing passage of a selected mass to charge ratio or limited mass to charge ratio range whilst excluding ions of other mass to charge ratios (m/z). The quadrupole mass filter 70 can be operated to allow passage of ions of a relatively wide mass to charge ratio range (e.g. 400-1210 amu), in particular for MS1 scans, which is useful for acquiring a wide range mass spectrum.

Ions then pass through a quadrupole exit lens/split lens arrangement 80 and into a transfer multipole 90. The transfer multipole 90 guides the mass filtered ions from the quadrupole mass filter 70 into a curved trap (C-trap) 100. The C-trap 100 has longitudinally extending, curved electrodes which are supplied with RF voltages and end cap electrodes to which DC voltages are supplied to provide potential barriers at the ends of the C-trap 100. The result is a potential well that extends along the curved longitudinal axis of the C-trap 100. In a first mode of operation, the DC end cap voltages are set on the C-trap so that ions arriving from the transfer multipole 90 are captured in the potential well of the C-trap 100, where they are cooled. The injection time (IT) of the ions into the C-trap determines the number of ions (ion population) that is subsequently ejected from the C-trap into the mass analyser. Whilst a C-trap 100 is used in the mass spectrometer of FIG. 1, in other embodiments, for example where a different type of mass analyser is used, different ion storage devices could be used instead, e.g. a linear trap with straight, not curved, electrodes.

Cooled ions reside in a cloud towards the bottom of the potential well and are then ejected orthogonally from the C-trap 100 towards an orbital trapping device 110 such as the Orbitrap® mass analyser sold by Thermo Fisher Scientific, Inc. The orbital trapping device 110 has an off centre injection aperture and the ions are injected into the orbital trapping device 110 as coherent packets, through the off centre injection aperture. Ions are then trapped within the orbital trapping device 110 by a hyperlogarithmic electric field, and undergo back and forth motion in a longitudinal direction whilst orbiting around the inner electrode.

The axial (z) component of the movement of the ion packets in the orbital trapping device 110 is (more or less) defined as simple harmonic motion, with the angular frequency in the z direction being related to the square root of the mass to charge ratio of a given ion species. Thus, over time, ions separate in accordance with their mass to charge ratio.

Ions in the orbital trapping device 110 are detected by use of an image detector (not shown in FIG. 1) which produces a "transient" in the time domain containing information on all of the ion species as they pass the image detector. The transient is then subjected to a Fast Fourier Transform (FFT) resulting in a series of peaks in the frequency domain. From these peaks, a mass spectrum, representing abundance/ion intensity versus m/z, can be produced.

In the configuration described above, the sample ions (more specifically, a subset of the sample ions within a mass range of interest, selected by the quadrupole mass filter) are analysed by the orbital trapping device 110 without fragmentation. The resulting mass spectrum is denoted MS1.

MS2 analysis (or, more generally, MS$^n$) can also be carried out by the mass spectrometer 10 of FIG. 1. To achieve this, precursor sample ions are generated and transported to the quadrupole mass filter 70 where a subsidiary mass range is selected. The ions that leave the quadrupole mass filter 70 are directed through the C-trap 100 to the fragmentation chamber 120. The fragmentation chamber 120 is, in the mass spectrometer 10 of FIG. 1, a higher energy collisional dissociation (HCD) device to which a collision gas is supplied. The potential applied to the fragmentation chamber 120 is such that precursor ions arriving into the fragmentation chamber 120 have sufficient energy that their collisions with collision gas molecules result in fragmentation of the precursor ions into fragment ions. The fragment ions are then ejected from the fragmentation chamber 120 back towards the C-trap 100, where they are once again trapped and cooled in the potential well. Finally, the fragment ions trapped in the C-trap are ejected orthogonally towards the orbital trapping device 110 for analysis and detection. The resulting mass spectrum of the fragment ions is denoted MS2.

Although an HCD fragmentation chamber 120 is shown in FIG. 1, other fragmentation devices may be employed instead, employing such methods as collision induced dissociation (CID), electron capture dissociation (ECD), electron transfer dissociation (ETD), photodissociation, and so forth.

The "dead end" configuration of the fragmentation chamber 120 in FIG. 1, wherein precursor ions are ejected axially from the C-trap 100 in a first direction towards the fragmentation chamber 120, and the resulting fragment ions are returned back to the C-trap 100 in the opposite direction, is described in further detail in WO-A-2006/103412.

The mass spectrometer 10 is under the control of a controller 130 which, for example, is configured to control the timing of ejection of the trapping components, to set the appropriate potentials on the electrodes of the quadrupole etc. so as to focus and filter the ions, to capture the mass spectral data from the orbital trapping device 110, control the sequence of MS1 and MS2 scans and so forth. It will be appreciated that the controller may comprises a computer that may be operated according to a computer program comprising instructions to cause the mass spectrometer to execute the steps of the method according to the present invention. Of course, in other embodiments, a mass spectrometer may comprise a fragmentation chamber arranged in a "fly through" configuration, where fragmented ions travel through the fragmentation chamber on to a further mass analyser, such as a linear ion trap, for MS2 analysis. For example, the Fusion Lumos Tribrid mass spectrometer from Thermo Fisher Scientific, Inc. comprises such a "fly through" fragmentation chamber.

It is to be understood that the specific arrangement of components shown in FIG. 1 is not essential to the methods subsequently described. Indeed, other arrangements for carrying out the DIA methods of embodiments of the present invention are suitable. For example, a multi-reflection time-of-flight (MR-ToF) mass analyser or a Fourier transform Ion Cyclotron Resonance (FT-ICR) mass analyser can be used instead of an orbital trapping mass analyser.

An embodiment of the method will now be described with reference to FIGS. 2 and 3.

The sample to be analysed contains sample molecules, including at least one target analyte of interest. Initially, an isotopologue of a target analyte of interest is added to the sample to be analysed. An isotopologue is an isotopically labelled molecule that differs from its parent molecule (the target analyte) in that at least one atom has a different number of neutrons. In some embodiments, the parent molecule may be a targeted endogenous peptide of interest (target analyte). Such targeted endogenous peptides may only be present in samples to be analysed, if present at all, in relatively low abundance, thereby making them challenging to detect using conventional DIA methodologies.

In particular, for a given sample, the retention time of a targeted analyte may not be known prior to performing the DIA methodology. As the targeted analyte may only be present in the sample in low quantities, it is challenging to determine the retention time using conventional methods. Accordingly, an isotopologue is added to the sample in a quantity that is sufficient to enable the isotopologue to be easily detected by mass analysis. In a preferred embodiment, the isotopologue is added to the sample in a known quantity sufficient to enable the isotopologue to be detected. The isotopologue accordingly provides an isotopically labelled internal standard. As the isotopologue has the same chemical structure as the target analyte of interest, the retention time of the isotopologue will be similar to or the same as the target analyte.

In some embodiments, a plurality of different isotopologues of target analyte of interest may be added to a sample.

Each isotopologue may have a different isotopic label relative to the target analyte of interest. The different isotopologues may be added to the sample in different known amounts.

The sample and isotopologue may be supplied from a liquid chromatography (LC) column as part of the exemplary apparatus described above (as shown in FIG. 1).

Figure 2:
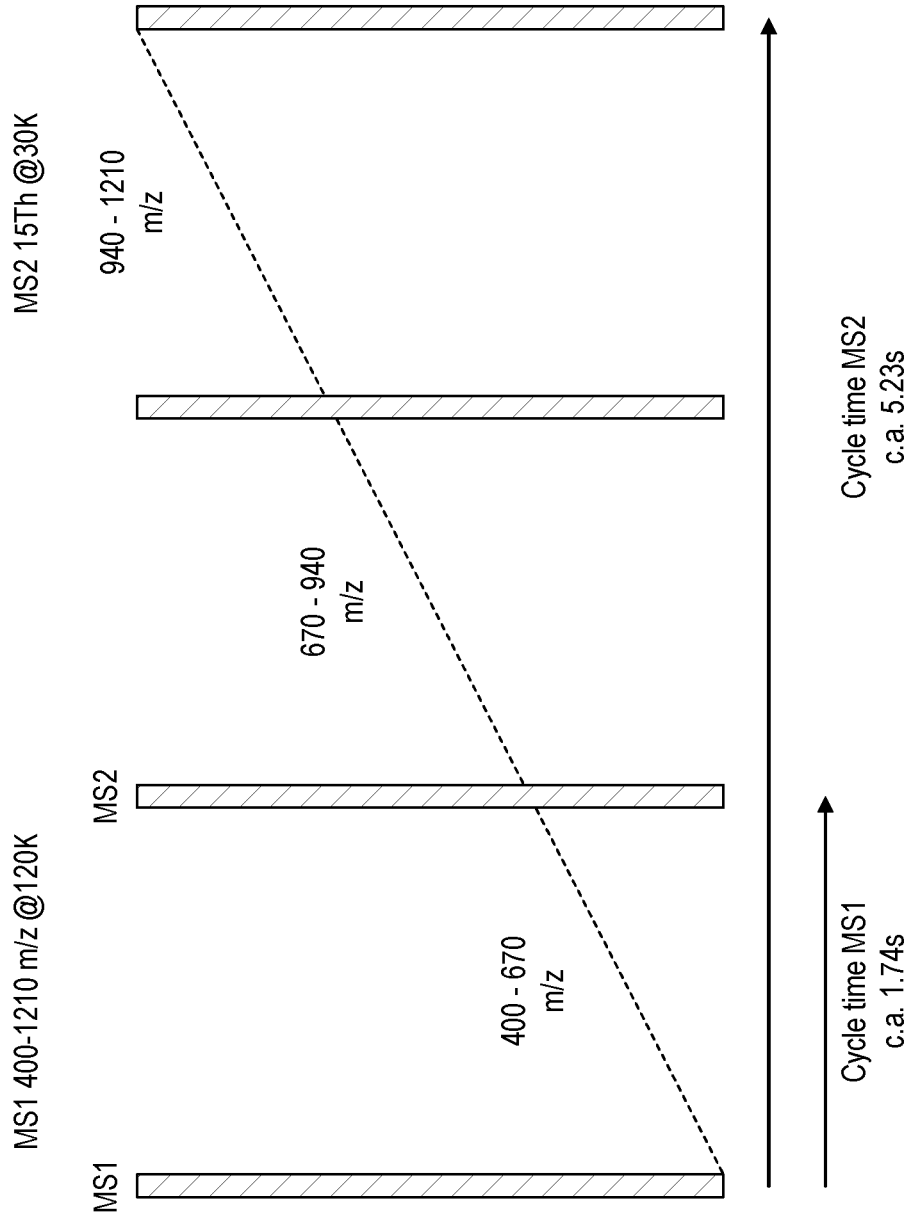
FIG. 2 shows a diagram of an example of a DIA methodology which may be performed in accordance with embodiments of the disclosure.
Figure 3:
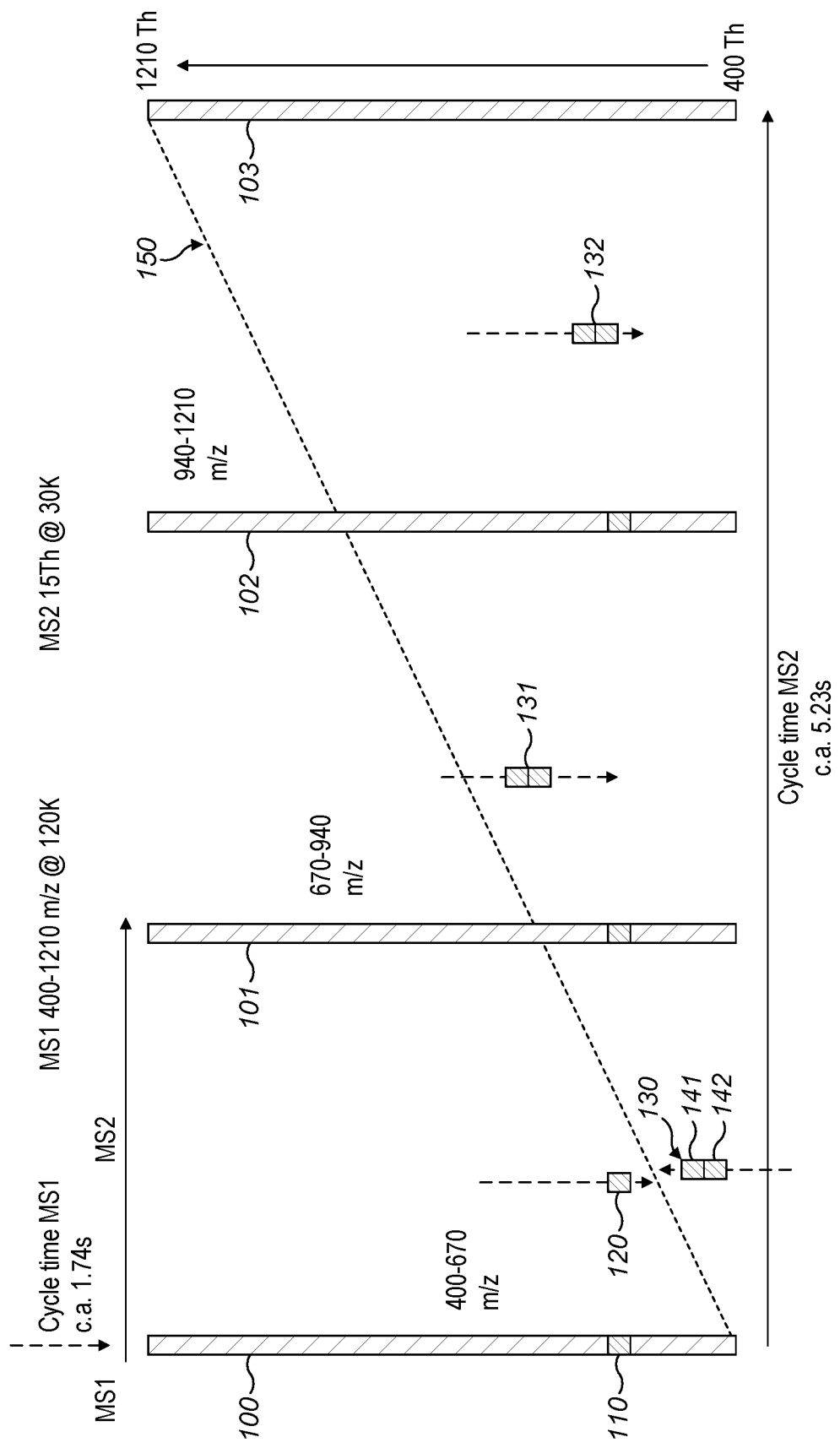
FIG. 3 shows a further diagram of a method of mass spectrometry in which target MS2 scans are performed in addition to a DIA methodology.

In the embodiment of FIGS. 2 and 3, the sample molecules and isotopologue molecules may be supplied from the LC column such that the data independent acquisition methodology according to embodiments of the present invention acquires data about the sample molecules and isotopologue molecules as they elute from the chromatography apparatus. It will be appreciated that over the course of an experiment the LC column may at times, only supply sample molecules, only supply isotopologue molecules, or supply sample molecules and isotopologue molecules to the mass spectrometer depending on the retention times of the sample molecules and isotopologue molecules. Reference to the supply of sample molecules and isotopologue molecules from the LC column in this disclosure will be taken to include any of the above cases.

According to methods of this disclosure, the mass spectrometer analyses the sample molecules and the isotopologue molecules according to a DIA methodology comprising MS1 scans and MS2 scans. Various DIA methodologies are known to the skilled person which may be performed in accordance with embodiments of this disclosure. As such, it will be appreciated that methods and mass spectrometers of the disclosure are not limited to any specific DIA methodology.

For example, FIG. 2 shows one example of a DIA methodology that may be performed in accordance with embodiments of this disclosure. FIG. 2 shows a single cycle of a DIA methodology. As shown in FIG. 2, with time on the horizontal axis and m/z on the vertical axis, a plurality of MS1 scans (represented by the vertical bars) and a set of MS2 scans (represented by the dots, which collectively make up the set of MS2 scans) are performed in a single cycle of the DIA methodology (workflow). The cycle shown in FIG. 2 includes performing one set of MS2 scans and a plurality (three) MS1 scans over a duration of around 5.23 s. MS1 scans may be performed using the apparatus shown in FIG. 1 (or other suitable apparatus).

In order to perform a single MS1 scan, sample molecules and/or isotopologue molecules elute from an LC column which are then ionized using the ESI source 20 to form precursor ions. The precursor ions (sample ions and/or isotopologue ions) subsequently enter the vacuum chamber of the mass spectrometer 10. The precursor ions are directed through capillary 25, RF-only lens 30, injection flatpole 40, bent flatpole 50 and into the quadrupole mass filter 70 in the manner as described above. The quadrupole mass filter 70 is controlled by the controller 130 to filter the precursor ions according to the selected precursor mass range of interest. A wide m/z range or window, e.g. >500 m/z units wide, such as a window 400-1200 m/z, is selected by the mass filter 70. In the embodiment of FIG. 2, the precursor mass range of interest for the MS1 scans is 400-1210 m/z.

Precursor ions then pass through the quadrupole exit lens/split lens arrangement 80, through the transfer multipole 90 and into the C-trap 100. From the C-trap 100, the precursor ions may be injected in to the orbital trapping mass analyser 110. Once the precursor ions are stabilised inside the orbital trapping mass analyser, the MS1 scan is performed by using the image current detector to detect the precursor ions present in the orbital trapping mass analyser 110. The detection of the precursor ions in the orbital trapping mass analyser 110 may be configured to be performed with a relatively high resolution for the MS1 scan (relative to the resolution of the MS2 scans).

According to the DIA methodology of FIG. 2, a set of MS2 scans are performed over the precursor mass range of interest during a DIA cycle. In order to perform a single MS2 scan of a mass range segment, eluting molecules from an LC column, which can be sample and/or isotopologue molecules depending on the retention time, are ionized to form precursor ions. The precursor ions are injected into the mass spectrometer in a similar manner to the MS1 scan. The precursor ions for the MS2 scan progress through the capillary 25, RF-only lens 30, injection flatpole 40, bent flatpole 50 and into the quadrupole mass filter 70 in a similar manner to the sample ions for the MS1 scan.

Once the precursor ions for the MS2 scan reach the quadrupole mass filter 70, the quadrupole mass filter 70 is controlled by the controller 130 to mass filter the precursor ions according to the relatively narrow mass range of the mass range segment being scanned (relative to the precursor mass range of interest). For example, in the embodiment of FIG. 2, the mass range of each mass range segment is 15 Th.

The (filtered mass segment) precursor ions pass from the quadrupole mass filter 70 through the C-trap 100 and towards the fragmentation chamber 120.

In the HCD fragmentation chamber 120, the high energy precursor ions collide with collision gas molecules which results in the fragmentation of the precursor ions into fragment ions. As such, the fragment ions may comprise fragmented sample ions and/or fragmented isotopologue ions. The fragment ions are then ejected from the fragmentation chamber 120 back into the C-trap 100 where they are trapped and cooled. The fragment ions are then ejected into the orbital trapping mass analyser 110 which is operated at a relatively lower resolution for analysis (MS2 scan), which enables a faster scan speed (shorter transient acquisition time). The resulting acquisition of a mass spectrum is denoted an MS2 scan.

According to the DIA methodology of FIG. 2, the controller 130 controls the mass spectrometer 10 to perform a set of MS2 scans over the mass range of interest. For the set of MS2 scans, the mass range of interest is divided into a plurality of mass range segments, each mass range segment covering a portion of the mass range of interest. For each mass range segment, the mass spectrometer 10 fragments the precursor ions within that mass range segment, and performs an MS2 scan of the fragmented precursor ions within the mass range segment. The mass spectrometer performs a MS2 scan for each mass range segment of the mass range of interest to make up a set of MS2 scans.

As shown in FIG. 2, the MS2 scans of the mass range segments are performed consecutively, starting at the lower limit of the mass range of interest. Of course, in other embodiments the MS2 scans forming the set of MS2 scans may be performed in a different order. For example, in some embodiments, the MS2 scans of the mass range segments may be performed consecutively starting at the upper limit of the mass range of interest, or in other embodiments, the MS2 scans may be ordered in a generally random or pseudo-random order.

According to the embodiment, the controller 130 controls the mass spectrometer 10 to perform DIA cycles comprising the plurality of MS1 scans over the mass range of interest, and also the set of MS2 scans.

The timing of the various stages of ionization, filtering, trapping, ejection, fragmentation (for MS2) and analysis, for each MS1 and MS2 scan, may be controlled by the controller 130 so as to optimise throughput. For example, it is possible to analyse precursor ions in the orbital trapping mass analyser 110 in order to obtain an MS1 scan, whilst a subrange of the precursor ions (mass range segment) is already in the fragmentation chamber 120 for fragmentation there. Alternatively, the fragment ions may be cooled and trapped in the C-trap 100 whilst analysis of the precursor ions is being carried out in the orbital trapping mass analyser 110, so that the fragment ions can be injected into the orbital trapping mass analyser 110 for obtaining an MS2 scan, as soon as the precursor ion analysis has been completed. During the time an MS1 scan is performed in the mass analyser 110, it may be possible to perform both the fragmentation of a mass segment of precursor ions as well as cooling and trapping the fragments in the C-trap 100 ready for injection into the mass analyser 110.

The MS1 scans may be repeated over the duration of the set of MS2 scans a number of times. Repeating the MS1 scans over the duration of the set of MS2 scans may result in the MS1 scans being repeated a number of time over the duration of a chromatographic peak of the sample ions, such that the chromatographic peak is sampled a number of times over its duration. For example, in the embodiment of FIG. 2, the MS1 scan is performed three times over the duration of a single set of MS2 scans. In some embodiments, the MS1 scans are performed such that a chromatographic peak of the sample ions is sampled at least 3 times, 5 times or 7 times. At least one DIA cycle is performed across a chromatographic peak. In some embodiments, at least two DIA cycles are performed across a chromatographic peak. In some embodiments, not more than two DIA cycles are performed across a chromatographic peak. Advantageously, by sampling a chromatographic peak a number of times in the MS1 domain, the number of data points over the peak is increased thereby improving the detection of precursor ions in the chromatographic peak. By sampling the peak a plurality of times, each of the precursor ions in the sample peak may be detected in a plurality of the MS1 scans leading to better quantitation precision.

As shown in FIG. 2, 3 MS1 scans are performed over the duration of a set of MS2 scans. As such, the MS1 scans are to be repeated at intervals of approximately 1.74 seconds (an MS1 sampling rate of ~0.57 Hz). The resolution for the MS1 scans is set to 120,000 across a mass range of interest of 400-1,210 m/z. For the mass spectrometer of FIG. 1, a detection time of a single MS1 scan performed at a resolution of 120,000 is about 256 ms. In some embodiments, the overheads between scans in the mass analyser 120 may be around 20 ms. Accordingly, the total duration for performing the three MS1 scans in the methodology of FIG. 2 may be around 828 ms.

In the DIA methodology of FIG. 2, the MS2 data is acquired for validation of the MS1 data, i.e. to confirm identification of sample molecules. As such, it is not required to obtain multiple sets of MS2 data over the duration of a chromatographic peak for quantitation purposes. Accordingly, a set of MS2 scans may be obtained over a longer duration (relative to the duration of a chromatographic peak, and the scan interval of the MS1 scans). As shown in FIG. 2, the performance of the MS1 scans are interleaved throughout the performing of a set of MS2 scans. In the example shown in FIG. 2, the mass range of interest is selected to be 400-1210 m/z, and the mass range for each of the segments is selected to be 15 Da. Therefore, 54 MS2 scans (not shown accurately in FIG. 2) may be performed in a single set of MS2 scans in the embodiment of FIG. 2. For example, in FIG. 2 the methodology uses a Q Exactive® HF apparatus as described above and so each MS2 scan may be acquired at a resolution of 30,000 in a detection time of around 64 ms with around 16 ms of overheads (total scan time around 80 ms). Accordingly, a single set of MS2 scans interleaved with a plurality of MS1 scans at the required MS1 sampling rate can be performed with a cycle time of around 5.2 seconds as shown in FIG. 2.

As discussed, the MS1 scans are interleaved about every 1.74 s between the MS2 scans, and the total time for performing a set of MS2 scans interleaved with the MS1 scans is about 5.23 s. 18 MS2 scans are sampled between each MS1 scan. This means the entire sequence in order to acquire a set of MS2 scans is: MS1 (400-1210 m/z), MS2 (400-415 m/z), MS2 (415-430 m/z) . . . MS2 (655-670 m/z), MS1 (400-1210 m/z), MS2 (670-685) . . . MS2 (925-940), MS1 (400-1210 m/z), MS2 (940-955) . . . MS2 (1195-1210).

Accordingly, a DIA methodology of an embodiment of the disclosure provides a series of MS1 scans with a high resolving power (e.g. 120,000) such that the MS1 scans may be used for quantitation of the precursor ions. The high mass accuracy contributed to the uniqueness of the precursor identifications. The MS2 scans of the fragmented precursor ions are used for validation of the precursor identification. A relatively large amount of time resolution is not required in the MS2 domain due to the high resolution quantitation performed in the MS1 domain, and therefore the MS2 scan may be optimised for only validation of the identity of the precursor ion. This approach allows for a data independent acquisition method of mass spectrometry which has improved sensitivity and selectivity. Furthermore, quantitation of precursor ions may be performed in the MS1 domain using a "library free" approach, thus reducing the requirements on post-processing of the acquired data.

One method for analysing DIA MS1 scan data and quantitating precursor ions using a library free approach is described in "DIA-Umpire: comprehensive computational framework for data independent acquisition proteomics", Tsou et al, Nat Methods, March 2015 p 258-264.

Of course, it will be appreciated that the above description of a DIA methodology is only one possible example of a DIA methodology. As such, the skilled person will appreciate that the present disclosure is not limited to the above DIA methodology, and that other methods of DIA may be used in conjunction with the target MS2 scans described below.

Figure 4:
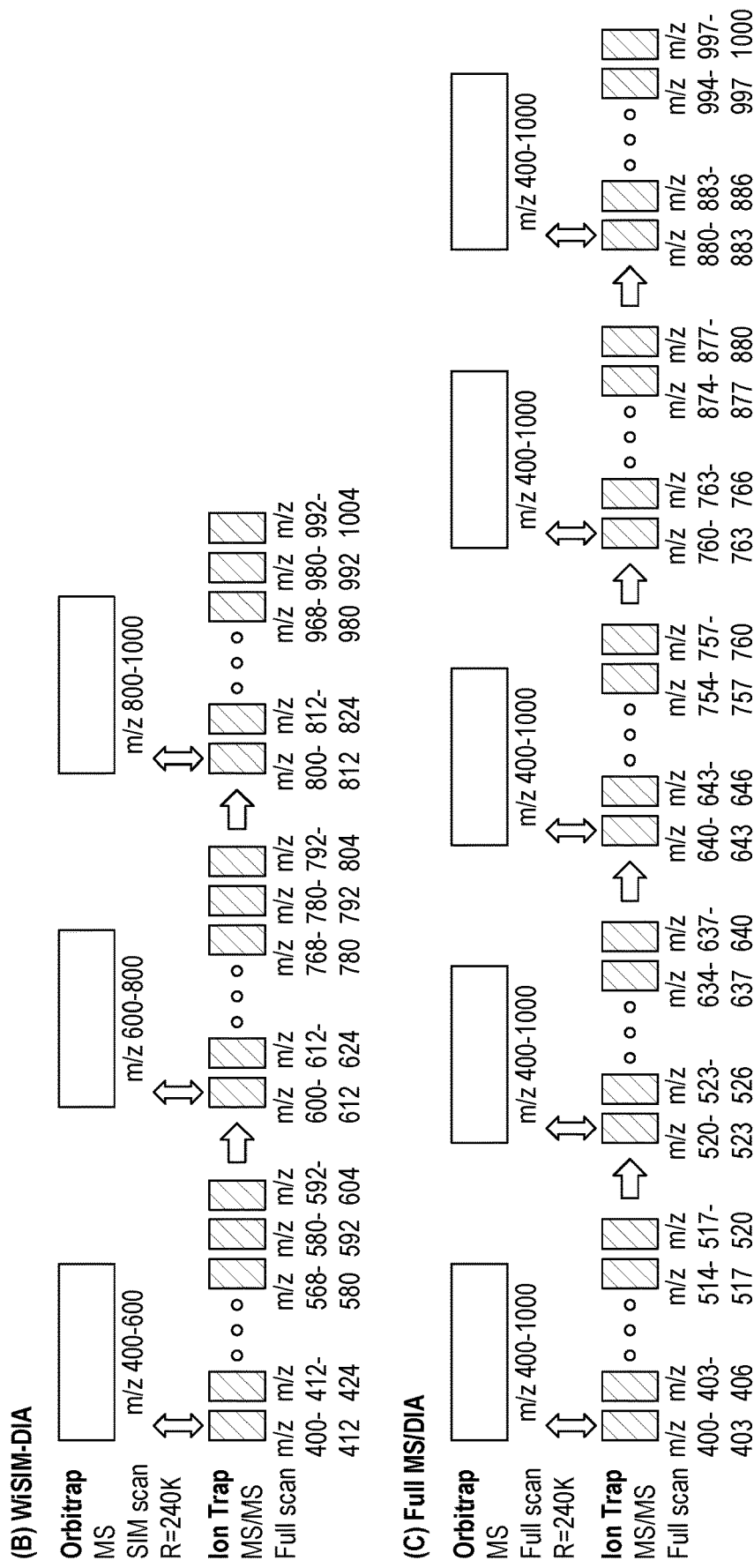
FIG. 4 shows diagrams of two further DIA methodologies which may be performed in embodiments of the disclosure.

For example, the DIA methodologies using a tribrid mass spectrometer (quadrupole-Orbitrap-Ion trap) disclosed in "Evaluation of Data-independent Acquisition (DIA) Approaches for Spiked Peptides in HeLa Digest on Q-OT-qIT Mass Spectrometer", Wei Zhang et al. (available at http://tools.thermofishercom/content/sfs/posters/PN-64122-Q-OT-qIT-ASMS2014-PN64122-EN.pdf) may be used. In those methodologies, an Orbitrap mass analyser can be used to perform MS1 scans of precursor ions, whilst a linear ion trap can be used to perform MS2 analysis of the fragmented ions. Examples of a single cycle of DIA methodologies as described in Zhang et al. are reproduced in FIG. 4. It will be appreciated that in accordance with embodiments of this disclosure, an isotopologue may be added to a sample to be analysed in accordance with these methodologies, wherein upon detection of the isotopologue, further target MS2 scans and optionally isotopologue MS2 scans may be performed as described herein.

Figure 5:
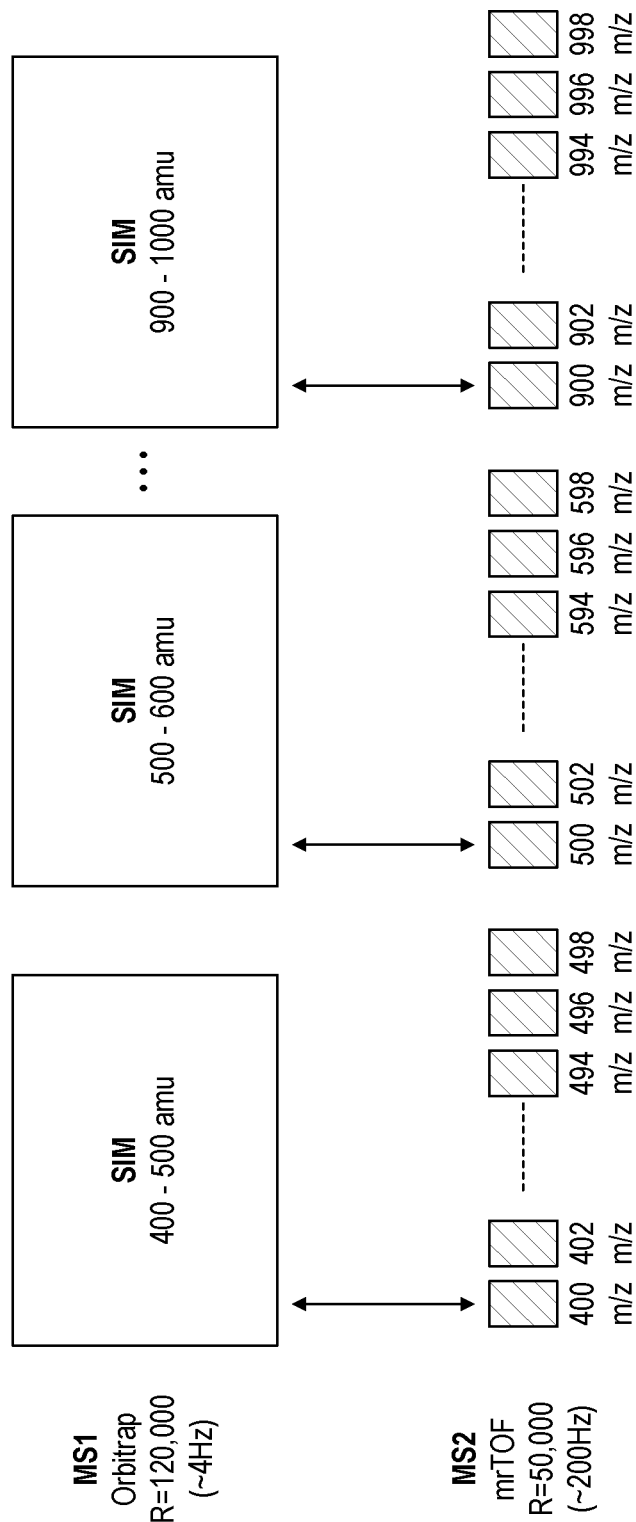
FIG. 5 shows a diagram of another DIA methodology which may be performed in an embodiment of the disclosure.

Similarly, the DIA methodologies disclosed in US 2018-0350576 A1 using an Orbitrap mass analyser to perform the MS1 scans and a ToF mass analyser to perform the MS2 scans may be used. For example, FIG. 5 shows a reproduction of a DIA methodology described further in US 2018-0350576 A1. It will be appreciated that in accordance with embodiments of this disclosure, an isotopologue may be added to a sample to be analysed in accordance with these methodologies, wherein upon detection of the isotopologue, further target MS2 scans and optionally isotopologue MS2 scans may be performed as described herein.

In addition to the DIA methodology described above, a method according to an embodiment of the disclosure seeks to identify when the isotopologue molecules are eluting from the chromatography system in order to perform additional target MS2 scans.

In some embodiments, the controller 130 may identify that isotopologue ions are eluting from the chromatography system by analysing the MS1 scan data for mass spectral peaks corresponding to the known mass to charge ratios of the added isotopologue ions. In some embodiments, the controller 130 may identify that isotopologue ions are eluting by analysing the MS1 scan data for mass spectral peaks corresponding to an isotopic pattern of the isotopologue ions. For example, in some embodiments, the controller 130 may be provided with a peptide sequence representative of the isotopologue in advance, since the identity of the target analyte is known. With the given peptide sequence, theoretical peptide isotopic patterns may be simulated for different charge states, e.g. 2+3+, and 4+. The theoretical m/z values for each charge states can be calculated.

The controller may analyse the MS1 scan data in real-time (on-the-fly matching) by comparing the theoretical peptide isotopic patterns to the mass spectral peaks of the MS1 data. When mass spectral peaks of the MS1 data match the theoretical peptide isotopic pattern within a predetermined error threshold, the controller 130 determines that the isotopologue (and thus the target analyte) is eluting from the chromatography apparatus. In some embodiments, a predetermined error threshold (mass error) of less than 5 ppm may be used.

According to the embodiment of FIG. 2, MS1 scans are repeated throughout the DIA methodology. Accordingly, the MS1 scans may be used to identify when the isotopologue is eluting from the chromatography apparatus. In some embodiments, the MS1 scans may be performed at a frequency of at least 0.5 Hz, in order to more accurately determine when the isotopologue begins to elute from the chromatography system. Of course, for other DIA methodologies, the MS2 scans may be used to identify if the isotopologue is eluting from the chromatography apparatus. As such, it will be appreciated that the embodiments of the present disclosure are not limited to using MS1 scan data to identity the isotopologue.

As an additional confirmatory test, the controller may also validate the presence of the isotopologue using the set of MS2 scans. It will be appreciated that the controller, having the structure, such as a peptide sequence, representative of the isotopologue, may generate an in silico MS2 mass spectrum for the isotopologue. This MS2 mass spectrum may be used for the on the fly matching or real time search. Thus, following identification of the isotopologue in the MS1 scan data, the next MS2 scan having a mass range segment covering the isotopologue may generate MS2 scan data which can be used to confirm the presence of the isotopologue.

Upon determining that isotopologue molecules are eluting from the chromatography system the controller 130 may interrupt the sequence of MS1 and MS2 scans forming the DIA methodology to perform a series of target scans. The series of target scans are performed in order to provide additional quantitation data for the target analyte. In the embodiment of FIGS. 2 and 3, the target scans are target MS2 scans. It will be appreciated that in other embodiments, the target scans may comprise target scans performed in the MS1 domain, for example target SIM scans. For example, the target scans performed may comprise a series of target MS2 scans, a series of target SIM scans, or a series of target MS2 scans and target SIM scans.

In the embodiment shown in FIG. 3, each target MS2 scan has an isolation window including a mass to charge ratio representative of the target analyte. The controller 130 may interrupt the sequence of MS1 and MS2 scans forming the DIA methodology repeatedly over the duration of a chromatographic peak of the isotopologue to perform further target MS2 scans. Accordingly, the target MS2 scans may provide additional MS2 scan data of the target for at least one of identification and quantitation of the target analyte. Thus, upon determining that isotopologue molecules are eluting from the chromatography system, a greater number of MS2 scans having an isolation window including a mass to charge ratio of the target analyte (target MS2 scans) may be performed over the duration of the chromatographic peak compared to the number of MS2 scans having an isolation window including a mass to charge ratio of the target analyte that are performed according to the sequence of MS2 scans forming the DIA methodology. The target MS2 scans may thus be performed out of sequence from the sequence of MS2 scans forming the DIA methodology.

The target MS2 scans are performed in addition to the MS1 and MS2 scans of the DIA methodology outlined above. As discussed above, the target MS2 scans are performed in order to aid the identification of target analytes which may only be present in the sample in a relatively low quantity. Accordingly, such target analytes may be difficult to detect using a conventional DIA methodology, as the mass spectra may be masked by more abundant species. Thus, in the methods of this disclosure, target MS2 scans are performed with an isolation window which includes the target analyte. The target MS2 scans performed may be highly targeted scans for identification and/or quantitation of the specific target analyte (i.e. attempting to exclude other possible constituents in order to improve the signal to noise ratio of the mass spectral peak of the target analyte ions).

In some embodiments, the target scans performed may comprise performing target scans in the MS1 domain. For example, in some embodiments target Selective Ion Monitoring (SIM) scans may be performed to provide additional quantitation data for the target analyte. For example, the mass spectrometer of FIG. 1 may be configured to perform additional target SIM scans following identification that the isotopologue is eluting from the chromatography apparatus. Similar to the target MS2 scans, precursor ions may be mass selected using the quadrupole mass filter 70. The quadrupole mass filter 70 uses a target isolation window including a mass to charge ratio representative of the target analyte to mass select the precursor ions. The mass selected precursor ions may then be transported to the mass analyser 110 for mass analysis in the MS1 domain.

For SIM scans, the target isolation window may be may be relatively narrow compared to the isolation windows used for the MS2 scans of the DIA methodology. In some embodiments the target SIM scans may have an isolation window including a mass charge ratio representative of the target analyte ion which is no greater than 5 Th wide. In some embodiments, the width of the target isolation window may be no greater than: 4 Th, 3 Th, or 2 Th. The target isolation window may be centred around an expected mass to charge ratio of an ion of target analyte. Using a relatively narrow target isolation window, the target SIM scans may be performed using a longer ion injection time of the precursor ions compared to the MS1 scans of the DIA methodology. For example, using the spectrometer shown in FIG. 1, a longer ion injection time may be used to inject precursor ions in the target isolation window into the C-trap 100 compared to the ion injection times used for the isolation windows for the MS1 scans of the DIA methodology.

Further to the above, the target scans of this disclosure may be performed in various ways, for example as set out in the options below.

A first option is to perform target scans, for example target MS2 scans of the target analyte using a target isolation window. The target isolation window may be relatively narrow compared to the isolation windows used for the MS2 scans of the DIA methodology. As such, in some embodiments the target MS2 scans may have an isolation window including a mass charge ratio representative of the target analyte ion which is no greater than 5 Th wide. In some embodiments, the width of the target isolation window may be no greater than: 4 Th, 3 Th, or 2 Th. The target isolation window may be centred around an expected mass to charge ratio of an ion of target analyte. Using a relatively narrow target isolation window, the target MS2 scans may be performed using a longer ion injection time of the precursor ions compared to the MS2 scans of the DIA methodology. For example, using the spectrometer shown in FIG. 1, a longer ion injection time may be used to inject precursor ions in the target isolation window into the C-trap 100 and/or fragmentation device 120 compared to the ion injection times used for the isolation windows for the MS2 scans of the DIA methodology.

The target MS2 scans may be repeated following identification of the isotopologue ions eluting from the chromatography system. The target MS2 scans may be performed with a frequency of at least 0.3 Hz or at least 0.5 Hz or around the same frequency as the MS1 scans. For example, in the embodiment of FIG. 3 the target MS2 130 scans may be repeated around every two seconds following identification of the isotopologue ions in the MS1 scan 100. The frequency of target MS2 scans 130, 131, 132 enables a more accurate quantitation of the target analyte and determination of the chromatographic peak shape.

In addition to performing target scans of the target analyte ions, the method may also comprise performing isotopologue scans of the isotopologue ions. The isotopologue scans may be performed to obtain additional quantitation data for the isotopologue. The isotopologue scans may be performed in the MS1 domain or the MS2 domain. For example, the isotopologue scans may comprise a series of isotopologue MS2 scans and/or a series of isotopologue SIM scans.

In the embodiment of FIG. 3, isotopologue MS2 scans may be performed. In such embodiments, the isotopologue MS2 scans are performed in addition to the MS1 and MS2 scans of the DIA methodology outlined above. Such isotopologue MS2 scans may have an isotopologue isolation window including a mass to charge ratio representative of the isotopologue ions. Similar to the target MS2 scans, the isotopologue MS2 scans may also have a relatively narrow isolation window which is no greater than 5 Th wide. In some embodiments, the width of the isotopologue isolation window of each isotopologue MS2 scan may be no greater than: 4 Th, 3 Th, or 2 Th. The isotopologue MS2 scans may have an isolation window which is substantially the same as the target MS2 scans. The isolation windows of the target MS2 scans and/or isotopologue MS2 scans may be narrower than the MS2 scans of the DIA methodology outlined above.

The isotopologue MS2 scans may be performed in a similar manner to the target MS2 scans. For example, for the mass spectrometer of FIG. 1, performing an isotopologue MS2 scan may comprise: mass selecting the precursor ions having a mass to charge ratio within the isotopologue isolation window using the quadrupole mass filter 70. The mass selected precursor ions may then be transferred to the fragmentation chamber 120 where the precursor ions within the isotopologue isolation window are fragmented to form isotopologue fragmented ions. The isotopologue fragmented ions may then be mass analysing the using the mass analyser 110.

As shown in FIG. 3, isotopologue MS2 scans may also be performed following identification of the isotopologue ions in the MS1 scan data. The isotopologue MS2 scans may be performed with a frequency of at least 0.3 Hz or at least 0.5 Hz. In some embodiments, the isotopologue MS2 scans may be repeated about every two seconds following identification of the isotopologue ions.

In some embodiments, the isotopologue MS2 scans may be performed with the same frequency as the target MS2 scans, or in other embodiments, the isotopologue scans may be performed with a different frequency. The isotopologue scans may be performed either before or after the target MS2 scans. The target MS2 scans (and optionally the isotopologue MS2 scans) may be repeated in order to obtain information suitable for characterising the chromatographic peak of the isotopologue molecules eluting from the chromatography apparatus. By repeating the target MS2 scans and/or the isotopologue MS2 scans with such frequency it may be possible to obtain data suitable for characterising the shape of the chromatographic peak. The target MS2 scans (and optionally the isotopologue MS2 scans) may be repeated until the isotopologue ions are no longer detected in the MS1 scan data. In other embodiments, the target MS2 scans (and optionally the isotopologue MS2 scans) may be repeated a predetermined number of times following identification of the isotopologue ions in the MS1 scan data, e.g. at least 2, 3, 4, 5, 6, 7, or 8 times, or more.

In some embodiments, a plurality of different isotopologues may be added to a sample in different amounts. For example, a first amount of a first isotopologue having a first mass, a second amount of a second isotopologue having a second mass, wherein the amounts and masses of the respective isotopologues differ. Upon identifying that at least one of the isotopologues is eluting from the chromatography system, the method comprises:

performing a plurality of first isotopologue MS2 scans having a first isotopologue isolation window including a mass to charge ratio representative of the first isotopologue;

performing a plurality of second isotopologue MS2 scans having a second isotopologue isolation window including a mass to charge ratio representative of the second isotopologue; and generating a quantitation calibration from the first isotopologue MS2 scans, the second isotopologue MS2 scans, and the target MS2 scans.

Of course, it will be appreciated that in some embodiments, more than two different isotopologues may be added to the sample which may be subsequently analysed in the MS2 domain during the method of mass spectrometry. Accordingly, a target analyte can be isotopically labelled in with a plurality of different isotopologues having different m/z, but still eluting at a similar time to the target analyte. By having two or more isotopologues with different known concentrations in the sample, a quantitation calibration, such as a calibration curve, can be determined as part of the method of mass spectrometry through isotope dilution analysis. It will be appreciated that in some embodiments of the disclosure the quantitation calibration may be generated as part of a post-processing step (i.e. after the sample has finished eluting from the chromatography apparatus). In other embodiments of the disclosure, the quantitation calibration may be generated in real time as the data from the mass analyser is generated.

By performing isotopologue scans independently of the target scans, the isotopologue ions may be analysed independently of the target analyte ions. This may be desirable for increasing the accuracy and signal to noise ratio of the target analyte ions signal in the target scan. Of course, it will be appreciated that the independence of the target scans and the isotopologue scans, comes at the expense of performing additional isotopologue scans which will increase the overall cycle time. In particular, for embodiments in which multiple target analytes may be partially co-eluting, the number of additional isotopologue scans performed may, in combination, result in a significant increase in cycle time.

A second option is to perform a target scan in which isotopologue ions and target analyte ions (if present) are mass analysed together in a single scan. For example, the single scan may be performed in the MS1 domain (e.g. a SIM scan) or in the MS2 domain (i.e. a MS2 scan). In such a target MS2 scan, the isolation window (a combined isolation window) used to mass select the ions may be chosen to define a continuous mass to charge range which includes mass to charge ratios representative of the target analyte ion and the isotopologue ion. In a target SIM scan, the isolation window (a combined isolation window) used to mass select the ions may be chosen to define a continuous mass to charge range which includes mass to charge ratios representative of the target analyte ion and the isotopologue ion.

In some embodiments, the width of a combined isolation window may be no greater than 8 Th. In other embodiments, the width of a combined isolation window may be no greater than 6 Th, or 4 Th.

It will be appreciated that the width of a combined isolation window might be broader than the target isolation window or isotopologue isolation windows used for the e.g. independent target MS2 scans and isotopologue MS2 scans of the first option described above, which could have an effect on the signal to noise ratio of the target analyte ions and isotopologue ions. Whilst the combined isolation window for such may be broader in some cases, it will be appreciated that the number of additional scans performed may be reduced relative to the first option.

A third option is to perform a target scan which is multiplexed with an isotopologue scan or a plurality of isotopologue scans (where a plurality of different isotopologues of a target analyte are added to the sample). For example, a target MS2 scan may be multiplexed with an isotopologue MS2 scan or a plurality of isotopologue MS2 scans (where a plurality of different isotopologues of a target analyte are added to the sample). A target SIM scan may be multiplexed with an isotopologue SIM scan or a plurality of isotopologue SIM scans (where a plurality of different isotopologues of a target analyte are added to the sample).

For a multiplexed target MS2 scan, a first group of precursor ions are mass selected using a first isolation window corresponding to a mass to charge ratio of a target analyte ion. The first group of precursor ions may be stored and/or fragmented in an ion trap, for example, in the C trap 100 or the fragmentation chamber 120 of the mass spectrometer of FIG. 1. A second group of precursor ions may then be mass selected using a second isolation window including a mass to charge ratio representative of an isotopologue ion. The second group of precursor ions may be stored and/or fragmented similarly to the first group. The first and second groups of precursor ions may then be fragmented together and the fragmented ions mass analysed together in a single multiplexed MS2 scan. Thus, by performing a multiplexed MS2 scan, a target analyte ion and at least one isotopologue ion are mass selected separately using different isolation windows and then a single multiplexed MS2 scan is performed for analysis of the mass selected target analyte ion and at least one isotopologue ion.

Multiplexing the target MS2 scan with the isotopologue MS2 scan may allow each of the first and second isolation windows to be relatively narrow (compared to the combined isolation window of the second option). In some embodiments, each of the first and second isolation windows may have a width of no greater than 5 Th. In some embodiments, the first and/or second isolation windows may have a width of no greater than: 4 Th, 3 Th, or 2 Th. It will be appreciated that in some embodiments, the widths of the first and second isolation windows may be different. By providing relatively narrow isolation windows for each of the isotopologue ions and target analyte ions to be analysed, the multiplexed target MS2 scans and isotopologue MS2 scan may have a relatively high sensitivity and relatively high selectivity for the multiplexed MS2 scan, similar to the first option.

By multiplexing the target MS2 scan with the isotopologue MS2 scan the number of additional MS2 scans performed may be reduced in a similar manner to the second option discussed above. As such multiplexing the target MS2 scans and the isotopologue MS2 scans may reduce the total cycle time of the method of mass spectrometry according to embodiments of this disclosure. It will be appreciated that multiplexing the MS2 scans may allow for two or more groups of ions to be mass selected with different isolation windows and combined in a single MS2 scan. As such multiplexed MS2 scans according to this disclosure may combine several isotopologue ions with different mass to charge ratios in a single MS2 scan. As discussed above, in some embodiments a plurality of isotopologues having different mass (e.g. a different number of neutrons) are added to the sample in different amounts. Upon identifying that at least one of the isotopologues is eluting from the chromatography system, a plurality of isotopologue MS2 scans may be performed. In some embodiments, a plurality of isotopologue MS2 scans may be performed for each of the isotopologues. As such, each of the plurality of isotopologue MS2 scans may have an isolation window corresponding to a respective mass to charge ratio of one of the isotopologue ions. It will be appreciated that the intensities of corresponding fragment peaks for each isotopologue MS2 scan will reflect the different amounts of the isotopologue added to the sample. A quantitation calibration may be generated from the different peak intensities of the isotopologue MS2 scans and based on the calibration a quantitation of the target analyte is determined from the intensity of one or more peaks in the target MS2 scans. In some embodiments, a plurality of different mass isotopologues of a target analyte can be added to the sample in different amounts so that they have different concentrations in the sample. The plurality of different mass isotopologues may differ in their nominal mass or exact mass.

A multiplexed MS2 scan may be used to analyse samples including a plurality of isotopologues of a target analyte. In some embodiments, a multiplexed MS2 scan may be performed by multiplexing the target MS2 scan with a plurality of isotopologue MS2 scans of the different mass isotopologues. The multiplexed MS2 scan may be performed substantially as described above, wherein third, fourth, fifth etc. groups of precursor ions are also included in the multiplexed MS2 scan. Since, the different mass isotopologues are present in different amounts or concentrations, a quantitation calibration curve from the intensities of the isotopologue and/or isotopologue fragment peaks can be generated from the multiplexed MS2 scan, which can be used to accurately quantify the target analyte in the sample from a single multiplexed MS2 scan.

A multiplexed target SIM scan may be performed in a following a similar concept to the multiplexed target MS2 scan. As such a first group of precursor ions are mass selected using a first isolation window corresponding to a mass to charge ratio of a target analyte ion. The first group of precursor ions may be stored in an ion trap, for example, in the C trap 100 or the fragmentation chamber 120 of the mass spectrometer of FIG. 1. A second group of precursor ions may then be mass selected using a second isolation window including a mass to charge ratio representative of an isotopologue ion. The second group of precursor ions may be stored similarly to the first group. The first and second groups of precursor ions may then mass analysed together in a single multiplexed SIM scan. Thus, by performing a multiplexed SIM scan, a target analyte ion and at least one isotopologue ion may be mass selected separately using different isolation windows and then a single multiplexed SIM scan is performed for analysis of the mass selected target analyte ion and at least one isotopologue ion.

In a fourth option, a real time search may be used to identify isotopologues, for example peptides, on the fly. This may be done by analysing the MS1 scan data for mass spectral peaks corresponding to the known mass to charge ratios of the added isotopologue ions or corresponding to an isotopic pattern of the isotopologue ions. Following identification of said isotopologues (peptides) a multiplexed-DIA scan may be triggered for quantitation.

FIG. 3 depicts an embodiment of a method of mass spectrometry that may be performed on the mass spectrometer shown in FIG. 1 and that exemplifies many of the above features.

In a first step of the method shown in FIG. 3, which is based on LC-MS analysis of a sample containing target analytes, the target analyte identities are input to the mass spectrometer and isotopologues of the target analytes are added to the sample. In this example, the target analytes are peptide sequences expected to be present in the sample. With the given peptide sequences, theoretical isotopic patterns with and without isotopic labelling are simulated for different charge states of the peptides, e.g. 2+3+, and 4+ using known methods. The theoretical m/z values for each charge state can be calculated.

In a second step, as the sample elutes from the chromatographic system, an MS1 scan 100 of the precursor mass range 400-1210 Th is performed. The theoretical precursor information about m/z values of mass spectral peaks and isotopic patterns from the first step is used for on-the-fly matching of the theoretical mass spectral peaks for the isotopologue to the mass spectral peaks acquired in the MS1 spectrum. The peak features of an isotopologue isotopic pattern and the accurate masses of the detected features in the MS1 may be considered matching if, for example, the mass error between them is less than 5 ppm and isotopic pattern matching is better than 80% based on the theoretical isotopic pattern. Optionally, a matching feature is put into an internal dynamic monitoring list for continuous monitoring in the upcoming MS2 DIA scans where the m/z values of the precursors are contained. In the example of FIG. 3, a precursor 110 m/z 500.5 (2+) of an isotopologue peptide is detected from the MS1 scan by matching.

In a third step, from the peptide sequence information, a theoretical MS2 spectrum can be generated in-silico, which is used for on-the-fly matching or real time searching by comparing the theoretical MS2 spectrum to the MS2 spectrum acquired in the DIA method for the detected precursor. When the DIA MS2 scan 120 is performed for the detected precursor mass (500.5 m/z) in the dynamic list of the second step, the fragments of the detected isotopologue peptide from its theoretical MS2 spectrum are compared to the peaks of the acquired DIA MS2 scan.

In the embodiment of FIG. 3, DIA MS2 scans forming part of the DIA methodology are performed in the sequence from the low mass to charge ratio to high mass to charge ratio following the analysis of the target analyte in the MS1 domain as part of the DIA methodology. Of course, in other embodiments, the DIA MS2 scan containing the isotopologue peptides may be prioritized and performed shortly after (e.g. immediately) after the MS1 scan where the peak features of an isotopologue isotopic pattern and the accurate masses of the detected features in the MS1 may be considered matching.

In a fourth step, when the DIA MS2 spectrum matches the theoretical MS2 spectrum of the isotopologue peptide of interest, the identification of the isotopologue peptide from the MS1 scan is confirmed. The MS2 matching criteria includes any or all of the number of matching fragments, the mass error of the fragments, and charge state of the fragments, etc. A narrow window multiplexed target MS2 scan 130 is then immediately triggered using separate isolation windows 141, 142 (each 2 m/z wide) for both the isotopologue peptide 141 and the corresponding endogenous target peptide 142. For the mass selection of the isotopologue peptide ions 141, the ion injection time is set to relatively low (e.g. 10 ms) as there is sufficient signal of the added-in isotopologue peptides. For the mass selection of the endogenous target peptide 142, to ensure the quantitation sensitivity, the ion injection time is set to relatively high (e.g. 100 ms). Accordingly, the total injection time of the isotopologue and endogenous peptides prior to fragmentation is set to approximately parallel the Orbitrap mass analyser detection time (e.g. 128 ms) to benefit the duty cycle speed.

In the embodiment of FIG. 3, the multiplexed MS2 scan is performed following the analysis of the target analyte in the MS2 domain as part of the DIA methodology. Of course, in other embodiments, the target MS2 scan (e.g. the multiplexed MS2 scan) may be prioritized and performed shortly after (e.g. immediately) after the MS1 scan where the peak features of an isotopologue isotopic pattern and the accurate masses of the detected features in the MS1 may be considered matching.

In a fifth step, after the first multiplexed target MS2 scan 130, the DIA scans continue according to the DIA methodology. As shown in FIG. 3, the DIA methodology comprises a plurality of MS2 scans 100, 101, 102, 103 and at least one set of MS2 scans 150. To ensure a good quantitation precision, at least 7-8 data points for the endogenous peptide are acquired from multiplexed target MS2 scans 130, 131, 132 across the chromatographic peak are triggered for the isotopologue and endogenous peptides 141, 142. Therefore, based on a typical chromatographic peak width for peptides of about 16 s, the multiplexed target MS2 scan of the same pair of isotopologue and endogenous peptides is repeated every 2 s, until the isotopologue peptide is no longer detectable in the MS1 full scan or the last multiplexed MS2 scan of a fixed number of multiplexed scans is acquired.

As noted above, in some embodiments of the disclosure, a DIA MS2 scan of a DIA methodology containing the isotopologue peptides may be prioritized and performed shortly after (e.g. immediately) after the MS1 scan where the peak features of an isotopologue isotopic pattern and the accurate masses of the detected features in the MS1 may be considered matching. Furthermore, in some embodiments, the target MS2 scan (e.g. the multiplexed MS2 scan) may be prioritized and performed shortly after (e.g. immediately) after the MS1 scan where the peak features of an isotopologue isotopic pattern and the accurate masses of the detected features in the MS1 may be considered matching. As such, it will be appreciated that in some embodiments, the target MS2 scan may be performed by modifying a MS2 scan of the DIA methodology. In order for the target MS2 scan to provide additional quantitation data for the target analyte, the target MS2 scan may have an increased injection time, and/or a narrower target isolation window relative to the unmodified DIA MS2 scan of the DIA methodology. As such, in this embodiment, target MS2 scans may be performed through a modification of a scheduled MS2 scan of the DIA methodology. In other embodiments, target scans may be performed in addition to the scheduled scans of the DIA methodology (i.e. additional target MS2 scans and/or additional target SIM scans).

Accordingly, embodiments of the present disclosure may be used to provide a method of mass spectrometry which follows a DIA methodology whilst also allowing for targeted identification and/or quantitation of one or more target analytes identified in advance. The method of mass spectrometry is particularly suitable for identification and/or quantitation of one or more target analytes that have a low abundance. In particular, the methods and embodiments of the present disclosure may be combined with a high resolution MS1-based quantitation DIA workflow which can deliver high confidence of identification and better precision of quantitation than approaches previously made in the art. The invention is of benefit in fields such as gene mutation detection, genome and/or proteome sequencing, cancer prognostic and/or diagnostic testing, known clinical markers detection and quantification, and drug response testing, for example.

The invention claimed is:

1. A method of mass spectrometry comprising:
adding an isotopologue of a target analyte to a sample;
ionising the sample and isotopologue as it elutes from a chromatography system to form precursor ions;
mass analysing the precursor ions using a data independent acquisition (DIA) methodology comprising performing mass analysis scans in a MS1 domain and performing mass analysis scans in a MS2 domain;
identifying that the isotopologue is eluting from the chromatography system; and
performing a plurality of target scans based on the identification that the isotopologue is eluting from the chromatography system, each target scan of the plurality of target scans having a target isolation window including a mass to charge ratio representative of the target analyte over a duration of a chromatographic peak of the isotopologue for at least one of identification and quantitation of the target analyte, wherein the target scans are configured to provide additional quantitation data for the target analyte.

2. A method according to claim 1, wherein the target scans are performed in at least one of the MS1 domain and the MS2 domain.

3. A method of mass spectrometry according to claim 1, wherein
identifying that the isotopologue is eluting from the chromatography system comprises identifying the isotopologue at least based on the mass analysis scans performed in the MS1 domain.

4. A method of mass spectrometry according to claim 1, wherein each target scan has a target isolation window which includes a mass to charge ratio representative of the target analyte and a mass to charge ratio representative of the isotopologue.

5. A method according to claim 1, wherein the plurality of target scans comprises a plurality of target MS2 scans and/or a plurality of Selected Ion Monitoring (SIM) scans.

6. A method of mass spectrometry according to claim 5, wherein performing each target MS2 scan comprises:
mass selecting the precursor ions having a mass to charge ratio within the target isolation window and fragmenting the precursor ions within the target isolation window to form target fragmented ions; and
mass analysing the target fragmented ions.

7. A method of mass spectrometry according to claim 1 wherein the method further comprises:
performing, based on the identification that the isotopologue is eluting from the chromatography system, isotopologue scans having an isotopologue isolation window including a mass to charge ratio representative of the isotopologue over the duration of a chromatographic peak of the isotopologue for quantitation of the isotopologue, wherein the isotopologue scans comprise at least one of a plurality of isotopologue MS2 scans and a plurality of isotopologue SIM scans.

8. A method of mass spectrometry according to claim 7, wherein performing each isotopologue MS2 scan comprises:
mass selecting the precursor ions having a mass to charge ratio within the isotopologue isolation window and fragmenting the precursor ions within the isotopologue isolation window to form isotopologue fragmented ions; and
mass analysing the isotopologue fragmented ions.

9. A method of mass spectrometry according to claim 7, wherein
each target MS2 scan is multiplexed with an isotopologue MS2 scan and/or each target SIM scan is multiplexed with an isotopologue SIM scan.

10. A method of mass spectrometry according to claim 9, wherein
multiplexing a target MS2 scan with an isotopologue MS2 scan comprises:
combining the precursor ions within the target isolation window for each target MS2 scan with the precursor ions within the isotopologue isolation window to form multiplexed precursor ions;
fragmenting the multiplexed precursor ions to form multiplexed fragmented ions; and
mass analysing the multiplexed fragmented ions.

11. A method of mass spectrometry according to claim 7, wherein
multiplexing a target MS2 scan with an isotopologue MS2 scan comprises:
fragmenting the precursor ions within the target isolation window for each target MS2 scan and fragmenting the precursor ions within the isotopologue isolation window;

storing the fragment ions from both windows together to form multiplexed fragmented ions; and mass analysing the multiplexed fragmented ions.

12. A method of mass spectrometry according to claim 9, wherein multiplexing a target SIM scan with an isotopologue SIM scan comprises:

combining the precursor ions within the target isolation window for each target SIM scan with the precursor ions within the isotopologue isolation window to form multiplexed precursor ions; and mass analysing the multiplexed precursor ions.

13. A method of mass spectrometry according to claim 7, wherein adding an isotopologue of a target analyte to the sample comprises:

adding a first amount of a first isotopologue of the target analyte having a first mass to the sample; and adding a second amount of a second isotopologue of the target analyte to the sample, the second amount and the second mass different being different to the first amount and the first mass respectively, wherein upon identifying that at least one of the first or second isotopologues is eluting from the chromatography system, the method comprises:

performing a plurality of first isotopologue scans having a first isotopologue isolation window including a mass to charge ratio representative of the first isotopologue;

performing a plurality of second isotopologue scans having a second isotopologue isolation window including a mass to charge ratio representative of the second isotopologue; wherein the first and second isotopologue scans are isotopologue MS2 scans and/or isotopologue SIM scans, and generating a quantitation calibration from the first isotopologue scans, the second isotopologue scans, and the target scans.

14. A method of mass spectrometry according to claim 13, wherein each target scan is multiplexed with a respective first and second isotopologue scan.

15. A method of mass spectrometry according to claim 1, wherein when performed, the target and/or the isotopologue scans are interleaved throughout the DIA methodology over the duration of the chromatographic peak of the isotopologue.

16. A method of mass spectrometry according to claim 15, wherein the target scans and/or the isotopologue scans are interleaved throughout the DIA methodology at intervals of no greater than 2 seconds.

17. A method of mass spectrometry according to claim 1, wherein the target isolation window for each target scan is no greater than 3 Th; and/or the isotopologue isolation window for each isotopologue scan is no greater than 3 Th.

18. A method of mass spectrometry according to claim 1 wherein mass analysing the sample using a data independent acquisition (DIA) methodology comprises:

performing a plurality of MS1 scans of the precursor ions; and performing a plurality of MS2 scans of the precursor ions.

19. A method of mass spectrometry according to claim 1, wherein mass analysing the sample using a DIA methodology comprises;

selecting a precursor mass range of interest for the sample to be analysed;

performing a plurality of MS1 scans, each of the MS1 scans comprising:

mass analysing the precursor ions across the precursor mass range of interest, using a mass analyser operated at a first, relatively higher resolution of at least 50,000 at m/z=200 amu, for identification and/or quantitation of the sample in the MS1 domain across the precursor mass range of interest; and performing a set of MS2 scans by:

segmenting the precursor mass range of interest into a plurality of precursor mass range segments, wherein for each precursor mass range segment:

fragmenting the precursor ions within that mass range segment, and performing an MS2 scan of the fragmented mass range segment with the mass analyser, operated at a second, relatively lower resolution, such that each of the fragmented sample segments across the precursor mass range of interest is fragmented and scanned in the MS2 domain, wherein the performing of the MS1 scans are interleaved throughout the performing of each of the sets of MS2 scans such that the MS1 scans provide a mass chromatogram of the sample.

20. A method of mass spectrometry according to claim 19, wherein at least 3, at least 5, or at least 7 MS1 scans are performed in the time taken to perform a set of MS2 scans.

21. A method of mass spectrometry according to claim 1, wherein at least one of the MS1 scans and the MS2 scans are performed using an orbital trapping mass analyser.

22. A mass spectrometer for performing data independent acquisition mass spectrometry on a sample to which an isotopologue of a target analyte is added, the mass spectrometer comprising:

an ionisation source for producing a plurality of precursor ions;

a mass analyser;

a fragmentation apparatus;

a mass selector;

a chromatography system configured to separate molecules of the sample upstream from the mass selector; and a controller configured:

to cause the ionisation source to ionise the sample and isotopologue as they elute from a chromatography system to form precursor ions;

to cause the mass spectrometer to mass analyse the precursor ions using a data independent acquisition (DIA) methodology comprising performing mass analysis scans in the MS1 domain and performing mass analysis scans in the MS2 domain; and to identify that the isotopologue is eluting from the chromatography system by analysing MS1 scan data for mass spectral peaks corresponding to the isotopologue, wherein upon the controller identifying that the isotopologue is eluting the controller is further configured to cause the mass spectrometer to perform a plurality of target scans each having a target isolation window including a mass to charge ratio representative of the target analyte over a duration of a chromatographic peak of the isotopologue for at least one of identification and quantitation of the target analyte, wherein the target scans are configured to provide additional quantitation data for the target analyte.

23. A computer program product comprising one or more non-transitory computer-readable media having computer instructions stored therein, the computer program instructions being configured such that, when executed by one or more computing devices, the computer program instructions cause the one or more computing devices to:
  cause an ionisation source to ionise a sample and an isotopologue as they elute from a chromatography system to form precursor ions;
  cause a mass spectrometer to mass analyse the precursor ions using a data independent acquisition (DIA) methodology comprising performing mass analysis scans in the MS1 domain and performing mass analysis scans in the MS2 domain; and
  identify that the isotopologue is eluting from the chromatography system by analysing MS1 scan data for mass spectral peaks corresponding to the isotopologue, wherein upon the controller identifying that the isotopologue is eluting the computer program instructions cause the one or more computing devices to:
  cause the mass spectrometer to perform a plurality of target scans each having a target isolation window including a mass to charge ratio representative of the target analyte over a duration of a chromatographic peak of the isotopologue for at least one of identification and quantitation of the target analyte,
  wherein the target scans are configured to provide additional quantitation data for the target analyte.

* * * * *